US009943995B1

(12) United States Patent
Staton et al.

(10) Patent No.: US 9,943,995 B1
(45) Date of Patent: Apr. 17, 2018

(54) THIN-WALLED ELASTIC PRODUCTS AND METHODS AND SYSTEMS FOR MANUFACTURING SAME

(71) Applicant: NEWTONOID TECHNOLOGIES, L.L.C., Liberty, MO (US)

(72) Inventors: Fielding B. Staton, Liberty, MO (US); David Strumpf, Columbia, MO (US)

(73) Assignee: Newtonoid Technologies, L.L.C., Liberty, MO (US)

( * ) Notice: Subject to any disclaimer, the term of this patent is extended or adjusted under 35 U.S.C. 154(b) by 0 days.

(21) Appl. No.: 15/604,384

(22) Filed: May 24, 2017

(51) Int. Cl.
*B29C 41/14* (2006.01)
*B29C 47/00* (2006.01)
*B29C 47/02* (2006.01)
*B29C 47/78* (2006.01)
*B29C 41/08* (2006.01)
*B29L 31/48* (2006.01)
*B29L 31/00* (2006.01)
*A61F 6/04* (2006.01)
*A41D 19/00* (2006.01)
*A41D 19/015* (2006.01)

(52) U.S. Cl.
CPC ............ *B29C 41/14* (2013.01); *B29C 41/085* (2013.01); *B29C 47/005* (2013.01); *B29C 47/0026* (2013.01); *B29C 47/025* (2013.01); *B29C 47/786* (2013.01); *A41D 19/0055* (2013.01); *A41D 19/0096* (2013.01); *A41D 19/01547* (2013.01); *A61F 6/04* (2013.01); *A61F 2006/048* (2013.01); *B29L 2031/4864* (2013.01); *B29L 2031/7538* (2013.01)

(58) Field of Classification Search
CPC ...... A61F 6/04; A61F 2006/048; B29C 41/14; B29C 41/085; B29C 47/005; B29C 47/0026; B29C 47/786; B29C 47/025; A41D 19/01547; A41D 19/0055; A41D 19/0096; B29L 2031/4864; B29L 2031/7538
USPC .................................................. 264/215, 305
See application file for complete search history.

(56) References Cited

U.S. PATENT DOCUMENTS 4,329,311 A * 5/1982 Moertel ................. A44B 19/14
264/285
4,852,586 A * 8/1989 Haines ...................... A61F 6/04
128/842

(Continued)

*Primary Examiner* — Jeffrey Wollschlager
(74) *Attorney, Agent, or Firm* — Lathrop Gage L.L.P.

(57) ABSTRACT

One method for creating barrier products (for example, condoms and gloves) includes: (a) dipping a former into a tank of elastic compound. The former has an indentation extending inwardly from an outer surface for creating a first protrusion on a first face of the barrier product. The method further includes: (b) removing the former from the tank of elastic compound, whereby some of the elastic compound removably adheres to the former and fills the indentation; (c) applying supplemental material to the elastic compound, whereby creating a second protrusion on a second face of the barrier product; and (d) fully drying the supplemental material. One barrier product includes an elastic wall having opposed faces, and first and second protrusions respectively extend from the opposed faces. The first and second protrusions are in cross-sectional alignment whereby rotational input forces on the first protrusion create rotational output forces on the second protrusion.

16 Claims, 10 Drawing Sheets

(56) References Cited

U.S. PATENT DOCUMENTS

| | | | | |
|---|---|---|---|---|
| 4,977,903 | A * | 12/1990 | Haines | A61F 6/04 128/842 |
| 9,492,953 | B2 * | 11/2016 | Brown | B29C 41/08 |
| 2003/0221239 | A1 * | 12/2003 | Modha | B29C 41/14 2/161.7 |
| 2007/0254106 | A1 * | 11/2007 | Olson | B29C 59/007 427/355 |
| 2007/0298184 | A1 * | 12/2007 | Connor | B01F 5/10 427/430.1 |
| 2012/0073580 | A1 * | 3/2012 | Chuah | A61F 6/04 128/844 |
| 2013/0013062 | A1 * | 1/2013 | Thompson | B29C 43/02 623/8 |
| 2013/0152943 | A1 * | 6/2013 | Nguyen | A61F 6/04 128/844 |
| 2013/0168446 | A1 * | 7/2013 | Coombes | A41D 19/0062 235/375 |
| 2014/0109917 | A1 * | 4/2014 | Nguyen | A61F 6/04 128/844 |
| 2015/0273518 | A1 * | 10/2015 | Varanasi | B29C 49/00 216/83 |
| 2015/0320586 | A1 * | 11/2015 | Nguyen | A61F 6/04 128/844 |
| 2017/0071271 | A1 * | 3/2017 | Megat Abdul Aziz | A41D 19/001 |

* cited by examiner

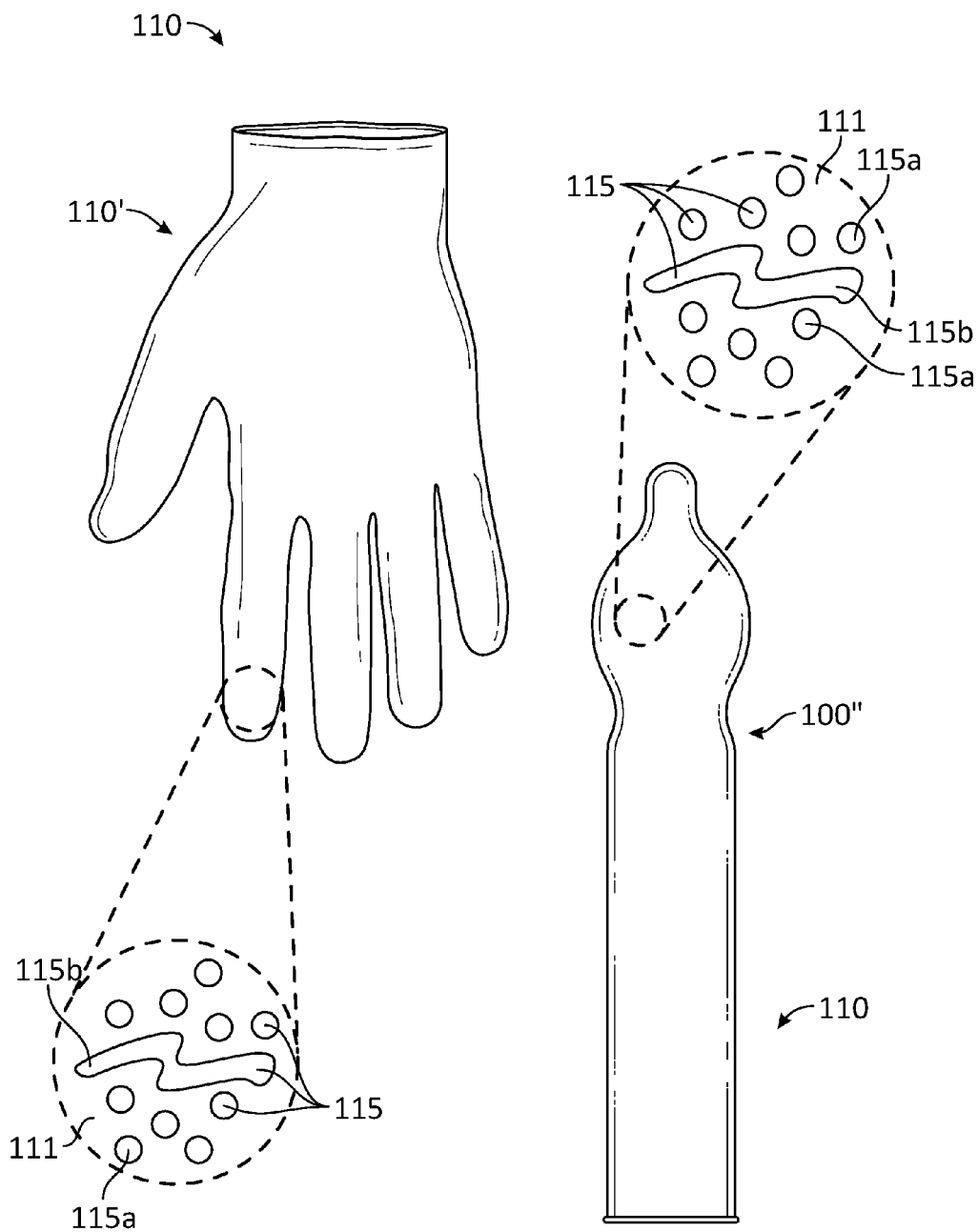

US 9,943,995 B1

THIN-WALLED ELASTIC PRODUCTS AND METHODS AND SYSTEMS FOR MANUFACTURING SAME

BACKGROUND

Thin-walled elastic products (or "barrier products") such as medical gloves and condoms are often constructed of latex or synthetic compounds such materials as polyurethane, polyisoprene, nitrile rubber, polyvinyl chloride, and neoprene. These products are often made by first creating a three-dimensional form (or "former"), generally constructed of ceramic or metal. The former is typically cleaned using various bleaching, rinsing, brushing, and drying processes, and is then dipped into a heated coagulant tank (e.g., consisting of calcium nitrate and calcium carbonate) to allow the latex or synthetic material to adhere—but not bind—to the former. The coagulant may be particularly necessary based on the material used for the former; for example, various latex and synthetic materials may not adhere directly to ceramics. The length of exposure in the coagulant tank may directly affect the wall thickness of the manufactured product. The dipped former is then heated, dipped into a tank of elastic (e.g., latex or synthetic) compound, and chilled. After or concurrent with being chilled, the former (with the latex or synthetic compound) may be dripped to ensure an even surface. After dripping, the former (again, with the latex or synthetic compound) may be cured in a dryer to further solidify. Proteins and other residuals may then be leached from the cured latex or synthetic material to lower the potential for an allergic reaction, and the finished product may be stripped from the former, tested to ensure compliance with product standards, and packaged.

While such manufacturing methods and systems have proven to be generally effective in creating impenetrable barrier products, these products typically result in substantially decreased tactile stimulation. Prior efforts to overcome this problem have typically focused on decreasing the wall thickness of the barrier product.

Embodiments of the current invention relate generally to thin-walled elastic products and systems and methods for making such products.

SUMMARY

The following presents a simplified summary of the invention in order to provide a basic understanding of some aspects of the invention. This summary is not an extensive overview of the invention. It is not intended to identify critical elements of the invention or to delineate the scope of the invention. Its sole purpose is to present some concepts of the invention in a simplified form as a prelude to the more detailed description that is presented elsewhere.

According to one embodiment, a method is provided for creating a barrier product. The method includes the step: (a) dipping a former into a tank of elastic compound. The former has an outer surface and an indentation, and the indentation extends inwardly from the outer surface for creating a first protrusion on a first face of the barrier product. The method further includes the steps: (b) removing the former from the tank of elastic compound, whereby some of the elastic compound removably adheres to the former with a portion of the removably adhered elastic compound filling the indentation; (c) applying supplemental material to the elastic compound removably adhered to the former, whereby creating a second protrusion on a second face of the barrier product; and (d) fully drying the supplemental material.

According to another embodiment, a method is provided for creating a barrier product. The method includes the step: (a) dipping a former into a tank of elastic compound. The former has an outer surface and an indentation, and the indentation extends inwardly from the outer surface for creating a first protrusion on a first face of the barrier product. The method further includes the steps: (b) removing the former from the tank of elastic compound, whereby some of the elastic compound removably adheres to the former with a portion of the removably adhered elastic compound filling the indentation; (c) producing a second protrusion on a second face of the barrier product; and (d) fully drying the elastic compound. Step (a) is performed before step (b), step (b) is performed before step (c), and step (c) is performed before step (d).

According to still another embodiment, a barrier product includes an elastic wall having opposed first and second faces, a first protrusion extending from the first face, and a second protrusion extending from the second face. The first and second protrusions are in cross-sectional alignment whereby rotational input forces on the first protrusion create rotational output forces on the second protrusion. Barrier products according to the current invention include, for example, condoms and gloves.

BRIEF DESCRIPTION OF THE DRAWINGS

FIG. 6 is a front view of a former for creating a glove according to an embodiment of the current invention, shown with magnification.

FIG. 7 is a front view of a former for creating a condom according to an embodiment of the current invention, shown with magnification.

FIG. 10b is a section view taken from FIG. 10a.

DETAILED DESCRIPTION

FIGS. 1 through 12b illustrate various methods and systems for manufacturing barrier products according to embodiments of the current invention, as well as barrier products according to embodiments of the current invention.

Figure 1:
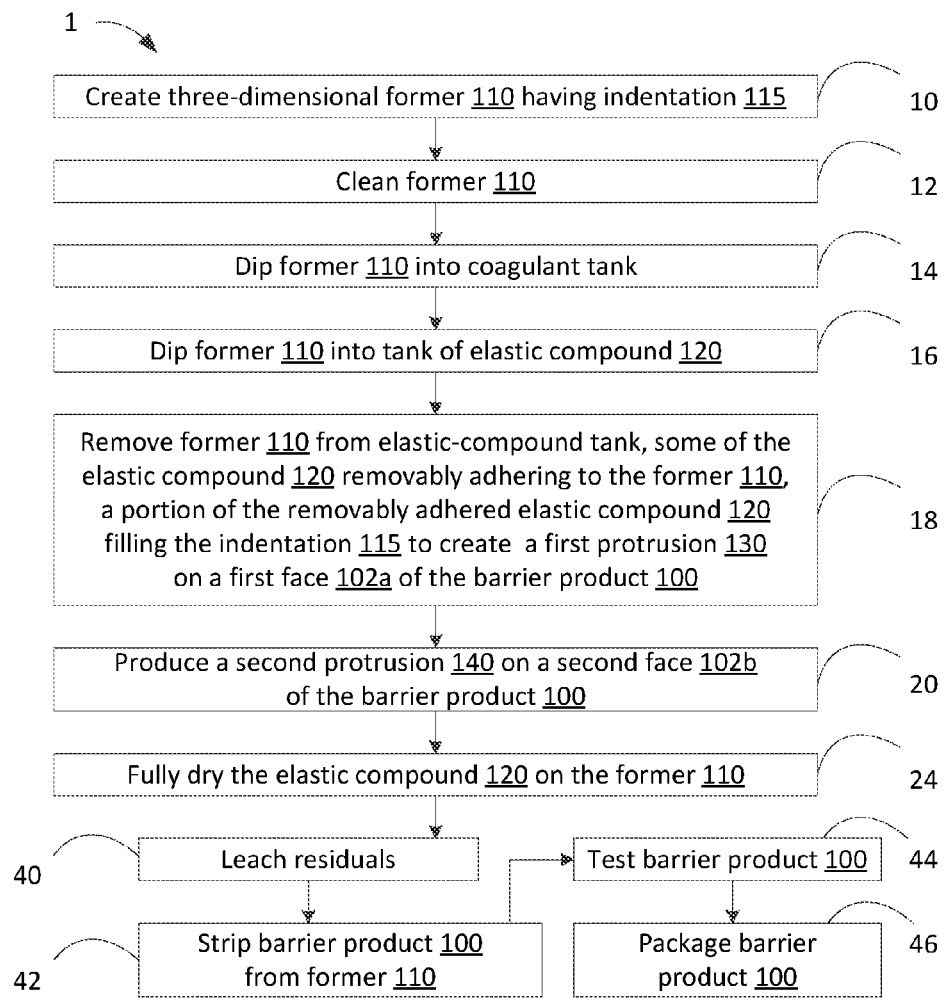
FIGS. 1 through 5 are flowcharts illustrating methods for creating barrier products according to embodiments of the current invention.
Figure 2:
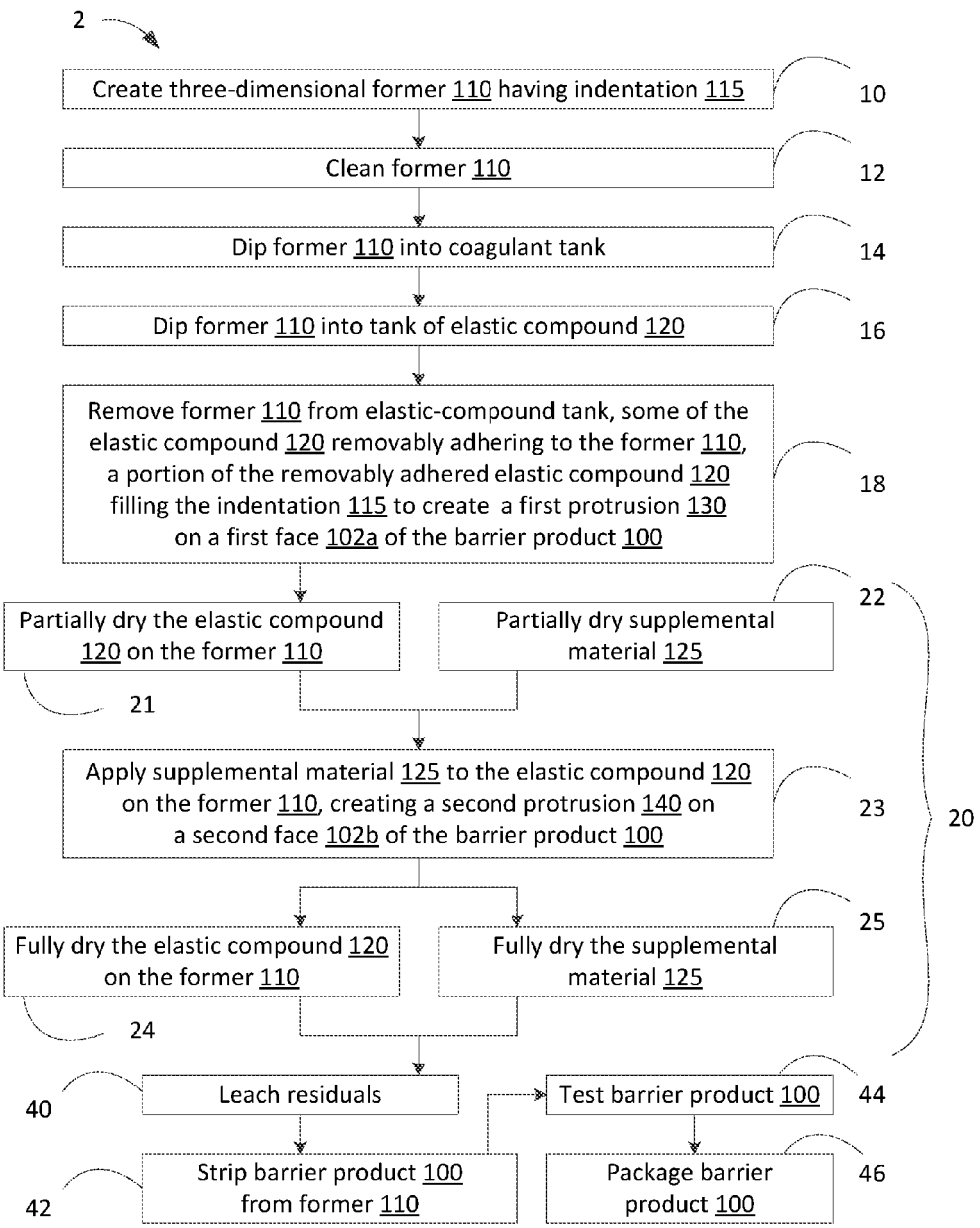
Figure 3:
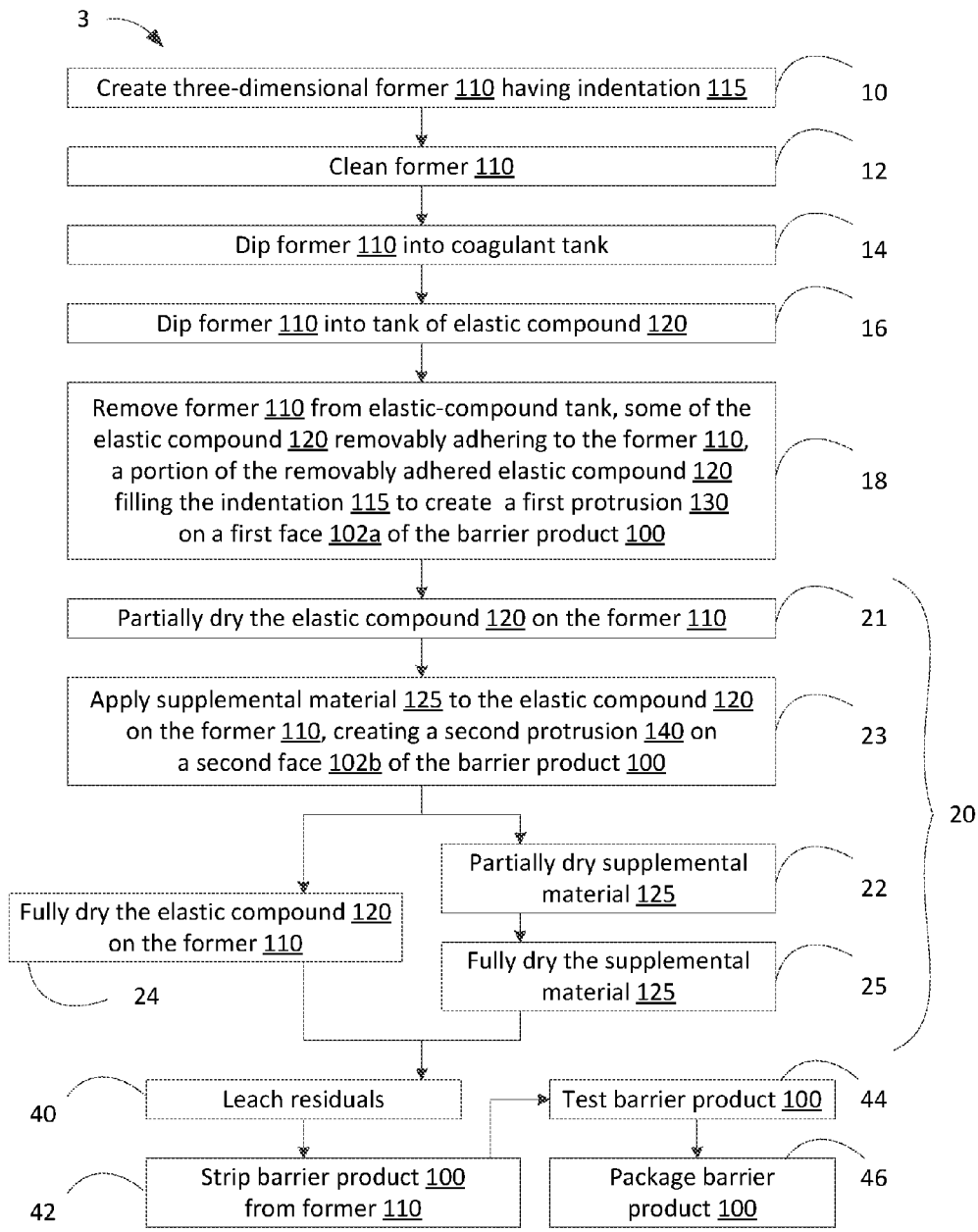
Figure 4:
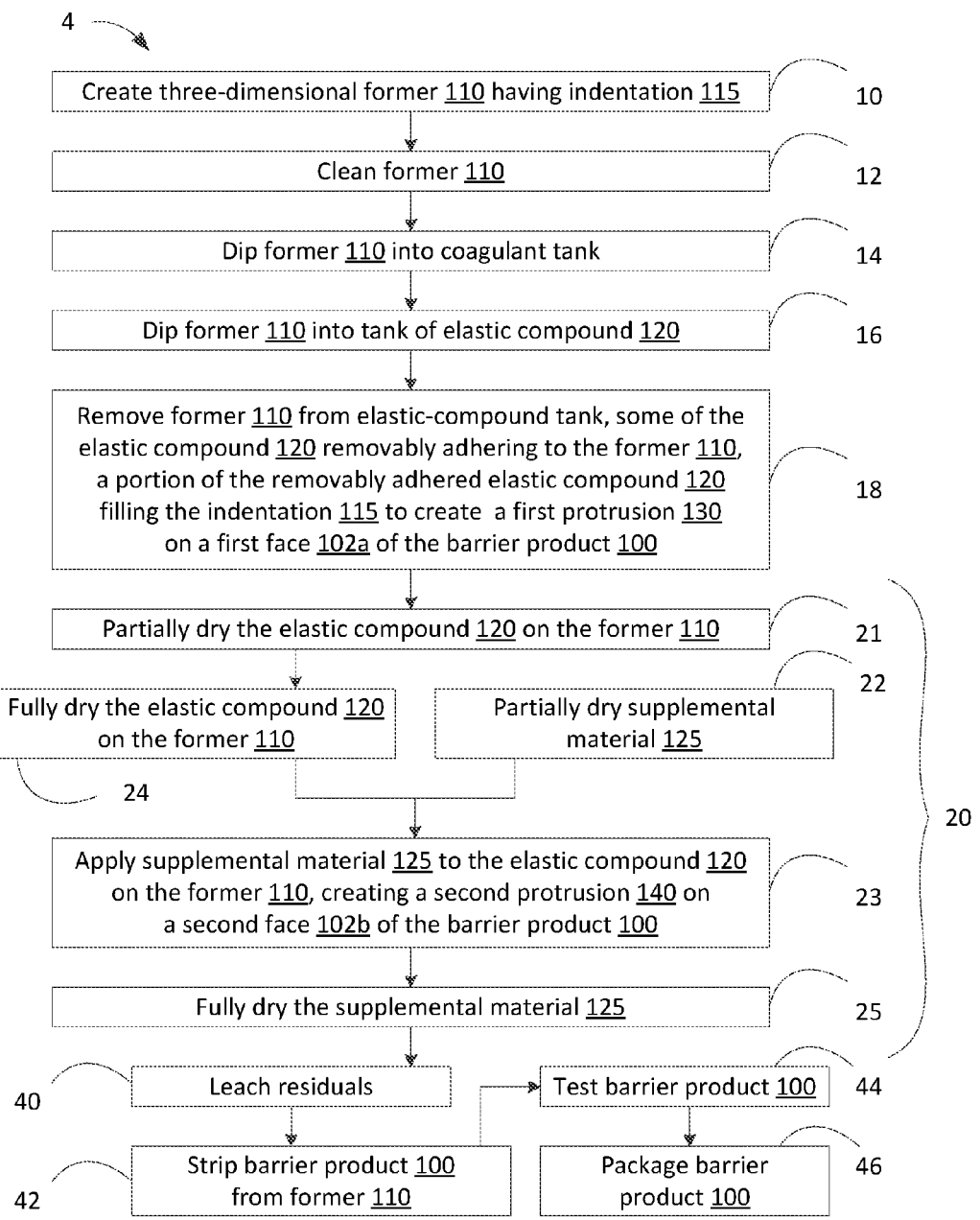
Figure 5:
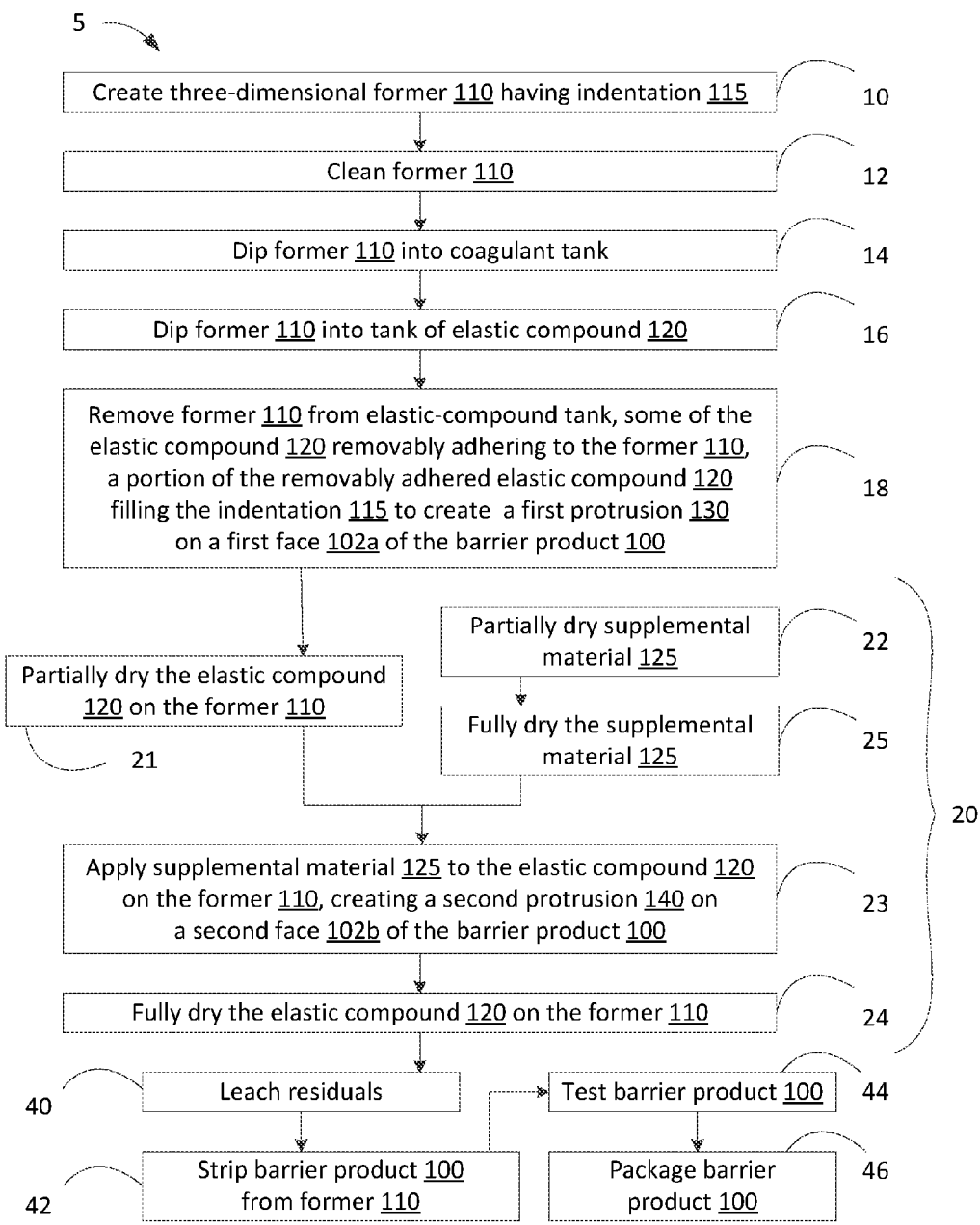
Figure 8:
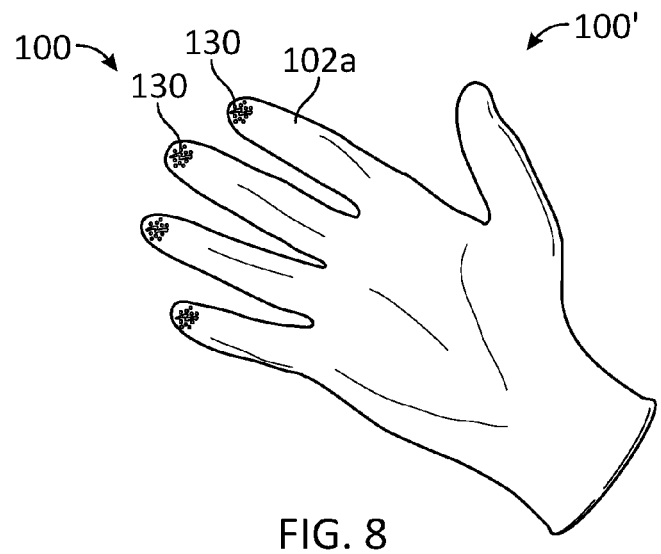
FIG. 8 is a front view of a glove according to an embodiment of the current invention.
Figure 9:
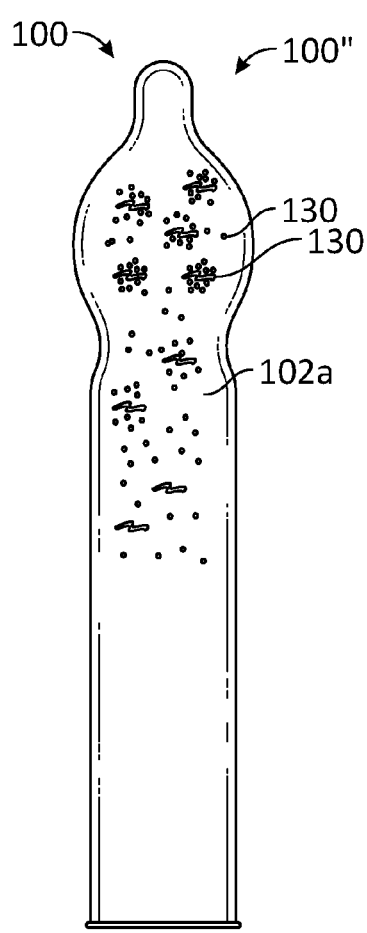
FIG. 9 is a front view of a condom according to an embodiment of the current invention.

FIG. 1 provides a method 1 for creating barrier products 100 (e.g., gloves 100' and condoms 100", shown in FIGS. 8 and 9). At step 10, a three-dimensional former 110 is created having an outer surface 111 and at least one indentation 115 extending inwardly from the outer surface 111. One former 110', for creating a glove 100', is illustrated in FIG. 6; another former 110", for creating a condom 100", is illustrated in FIG. 7; and still other types of barrier products 100 may be constructed using different formers 110. The former 110 may be constructed of ceramic, metal, glass, or any other appropriate material, and the indentations 115 may be generally cylindrical, or of any other desired shape (e.g., rings, waves, ovals, et cetera). FIGS. 6 and 7 show some cylindrical indentations 115a and some indentations 115b shaped as irregular waves. After the desired former 110 is obtained at step 10, the method 1 proceeds to step 12.

At step 12, the former 110 is cleaned. Debris on the former 110 may result in low-quality products, as is well understood. Cleaning is thus well known in the art, and may for example include various bleaching, rinsing, brushing, and drying processes (whether now existing or later developed). The method 1 continues from step 12 to step 14.

At step 14, the former 110 is dipped into a heated coagulant tank. It is well known in the art that various elastic compounds do not adhere to some materials which are often used to make formers, such as ceramics, and that coagulant materials may be used to allow elastic materials to adhere—but not bind—to a former. Calcium nitrate, calcium carbonate, and any other appropriate material (whether now existing or later developed) may be used in the coagulant tank. And, in some embodiments, step 14 may be omitted if the selected elastic compound appropriates adheres to the former 110 without coagulant material. The method 1 proceeds from step 14 to step 16.

At step 16, the former 110 is dipped into a tank of elastic compound 120. The elastic compound 120 may be any appropriate natural or synthetic compound, whether now existing or later developed. Example elastic compounds include latex, polyurethane, polyisoprene, nitrile rubber, polyvinyl chloride, silicone, and neoprene.

Figure 10A:
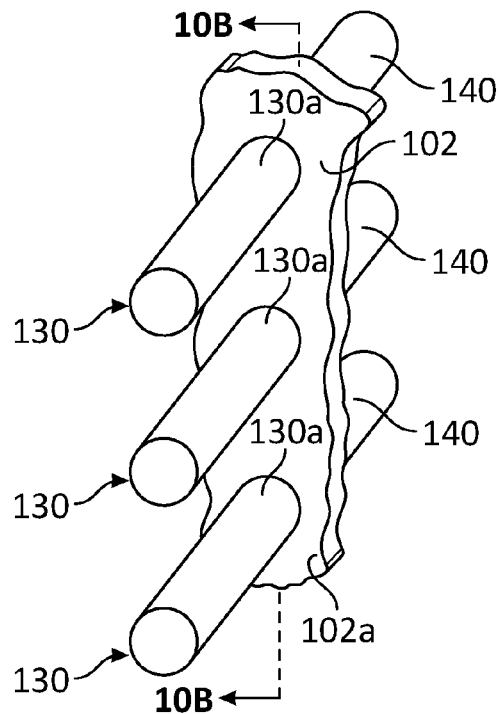
FIG. 10a is a perspective view of part of a barrier product according to an embodiment of the current invention.
Figure 10B:
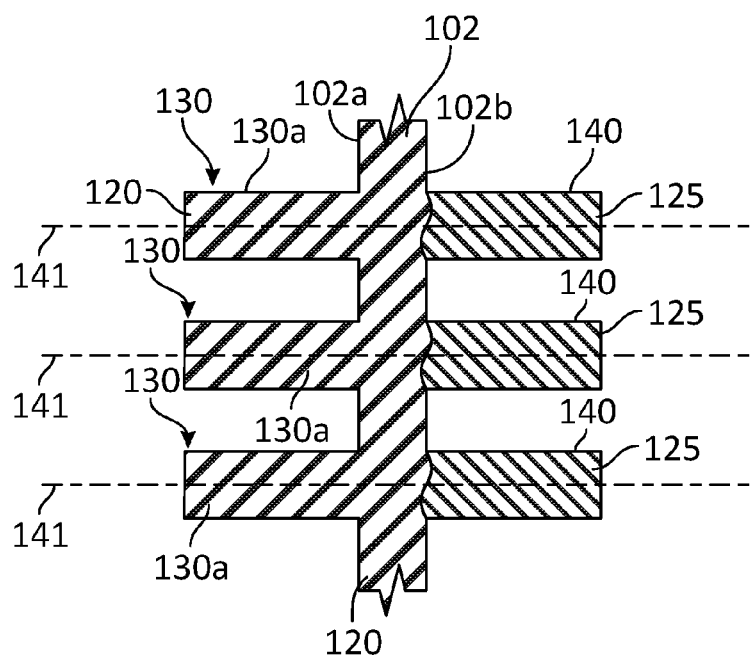
Figure 11A:
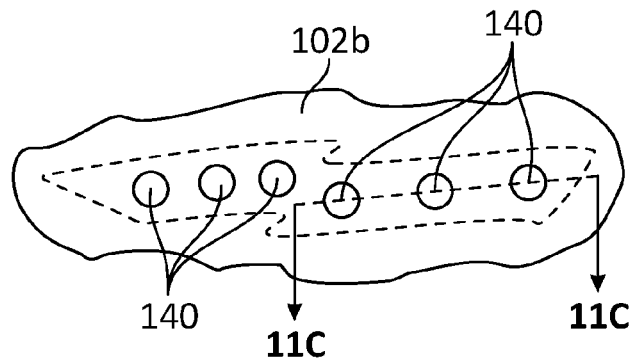
FIGS. 11a and 11b are front and rear views of part of a barrier product according to another embodiment of the current invention.
Figure 11B:
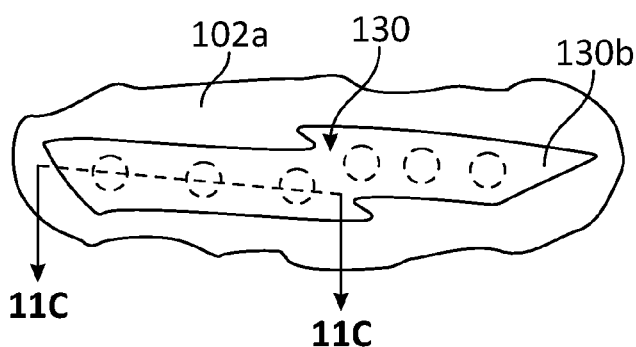
Figure 11C:
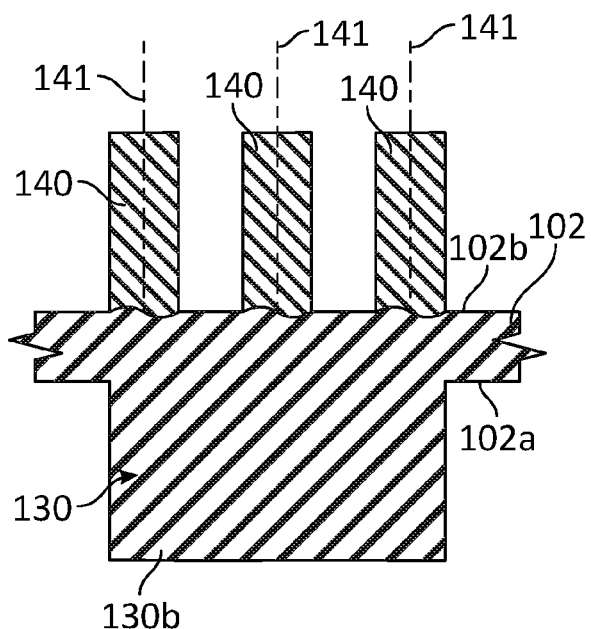
FIG. 11c is a section view taken from FIGS. 11a and 11b.
Figure 12A:
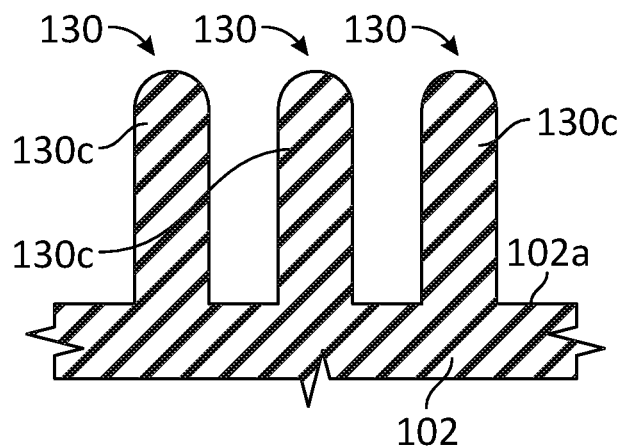
FIG. 12a is a section view of part of a barrier product according to still another embodiment of the current invention.
Figure 12B:
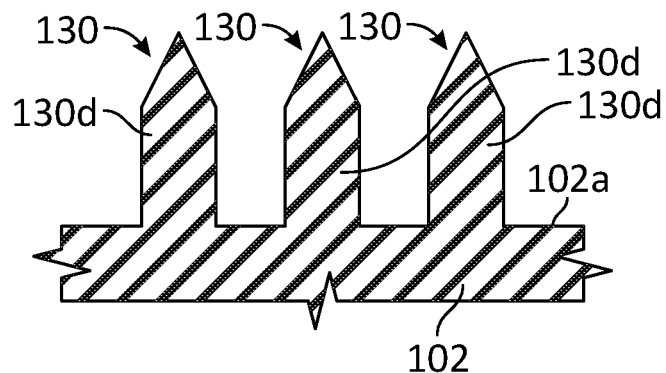
FIG. 12b is a section view of part of a barrier product according to yet another embodiment of the current invention.

After the former 110 is dipped at step 16, the former 110 is removed from the elastic-compound tank at step 18. Some of the elastic compound 120 removably adheres to the former 110 (via the coagulant material), and a portion of that removably adhered elastic compound 120 fills the indentation 115 to create a first protrusion 130 on one face 102a of the barrier product 100 (i.e., on face 102a of elastic wall 102). Of course many first protrusions 130 may be created, matching the number of indentations 115 in the former 110, and the first protrusions 130 will be shaped like the indentations 115. Cylindrical first protrusions 130a are shown in FIGS. 10a and 10b, and an irregular wave first protrusion 130b is shown in FIGS. 11b and 11c. FIGS. 12a and 12b illustrate other first protrusions 130 having different shapes. First protrusion 130c having a cylindrical portion and a domed tip is shown in FIG. 12a, and first protrusion 130d having a cylindrical portion and a conical tip is shown in FIG. 12b.

After step 18, at least one second protrusion 140 is produced on a second face 102b (FIGS. 10b, 11a, and 11c) of the barrier product 100 (i.e., on face 102b of the elastic wall 102). This is illustrated in FIG. 1 at step 20. Production of the second protrusion 140 may be accomplished in various ways and may take various shapes (e.g., cylindrical, rings, waves, ovals, et cetera), as set forth in more detail below. In some embodiments, it may be particularly desirable for the second protrusion 140 to be in cross-sectional alignment with at least one of the first protrusions 130. For example, FIGS. 10a and 10b show cylindrical first and second protrusions 130, 140 in cross-sectional (and axial) alignment, and FIGS. 11a through 11c show a wave-shaped first protrusion 130 and cylindrical second protrusions 140 in cross-sectional alignment. The terms "first" and "second" are merely used herein for convenience to discuss the protrusions on the opposed faces of the barrier products 100.

The method 1 is shown continuing from step 20 to step 30, where the elastic compound 120 is fully dried on the former 110. While steps 10, 12, 14, 16, and 18 remain generally consistent throughout the illustrated methods 1, 2, 3, 4, and 5, the timing of step 30 varies depending on the specific way that the second protrusion 140 is produced. And even in the method 1, step 30 may occur before, or as part of, step 20. Again, more information about producing the second protrusion 140 is provided below.

After the elastic compound 120 is fully dried on the former 110 and the second protrusion is created, residuals are leached at step 40. The barrier product 100 is then stripped from the former 110, tested, and packaged at steps 40, 42, 44, and 46. With the barrier product 100 packaged, the method 1 ends. Leaching, stripping, testing, and packaging are well known in the art and remain generally consistent throughout the illustrated methods 1, 2, 3, 4, and 5.

FIGS. 2 through 5 illustrate more specific methods 2, 3, 4, and 5 of creating the barrier product 100, with each of the methods 2, 3, 4, and 5 adding supplemental material 125 to create the second protrusion 140. Of course multiple second protrusions 140 may be created, as desired. In some embodiments, the supplemental material 125 may be selected to be the same material as the elastic compound 120. In other embodiments, the supplemental material 125 may differ, in whole or in part, from the elastic compound 120. It may be particularly desirable for the second protrusion 140 to permanently bond to the elastic wall 102, and for rotational input forces on the first protrusion 130 to create rotational output forces on the second protrusion 140—as this may enhance the resonance transfer to the user. Thus, in addition to forming and aligning the protrusions 130, 140 as disclosed, the materials 120, 125 (whether the same or different) may be selected to achieve these goals. Steps 10, 12, 14, 16, 18, 40, 42, 44, and 46 in the methods 2, 3, 4, and 5 are the same as in the method 1.

In the method 2, the elastic compound 120 on the former 110 is partly dried at step 21, the supplemental material 125 is partly dried at step 22, and the partly-dried supplemental material 125 is applied to the partly-dried elastic compound 120 on the former 110 to create the second protrusion 140 at step 23. It may be particularly desirable for an applicator to be used which does not touch the partly-dried elastic compound 120 on the former 110. Appropriate applicators may project (e.g., spray), press, roll, or otherwise apply the supplemental material 125 onto the partly-dried elastic compound 120 on the former 110 to create the second protrusion 140. By being partly dried before being applied, the supplemental material 125 may be easily formed into and maintain its desired shape (e.g., cylindrical, cylindrical with a domed or conical tip, pyramidal, domed, conical, et cetera). Similarly, the elastic wall 102 may generally maintain its desired shape and thickness by being partly dried before receiving the supplemental material 125. Nevertheless, in the method 2, the elastic wall 102 and the second projection 140 are not fully dried (at steps 24 and 25) until after the supplemental material 125 is applied at step 23, allowing the elastic wall 102 and the second projection 140 to meld together. If desired, the elastic wall 102 may be initially formed with an increased thickness to ensure a desired final thickness. For example, it may be desirable for the elastic wall 102 to have a final thickness of 3.5 mil to 14 mil for the glove 100' or a thickness of 2 mil to 3 mil for the condom 100". Desirability of increasing the initial wall thickness in this way may depend, for example, on the amount of drying before step 23, the amount of force received by the elastic wall 102 during step 23, the materials selected for the elastic compound 120 and the supplemental material 125, and the alignment of the protrusions 130, 140 (cross-sectional alignment increases the amount of elastic compound 120 adjacent the supplemental material 125). Moreover, an adhesive material may be applied to the elastic wall 102 and/or the second projection 140 before or during step 23. The addition of adhesive may also depend, for example, on the amount of drying before step 23, the amount of force received by the elastic wall 102 during step 23, and the materials selected for the elastic compound 120 and the supplemental material 125.

Turning now to the method 3 (FIG. 3), the method 3 primarily differs from the method 2 in the order of step 22. In the method 3, the supplemental material 125 is not partially dried (step 22) before being applied to the elastic wall 102 at step 23—and is instead dried after being applied to the elastic wall 102 at step 23. Applying the supplemental material 125 in this way (before being partially dried) may for example be useful with some materials 120, 125 to increase the bonding between the wall 102 and the second protrusion 140.

Method 4 (FIG. 4) primarily differs from the method 2 in the order of step 24. In the method 4, the elastic wall 102 is fully dried (step 24) before the supplemental material 125 is applied at step 23. Applying the supplemental material 125 in this way (after the elastic compound 120 on the former 110 is fully dried) may for example be useful with some materials 120, 125 to ensure the integrity of the elastic wall 102.

Method 5 (FIG. 5) primarily differs from the method 2 in the order of step 25. In the method 5, the supplemental material 125 is fully dried (step 25) before being applied to the elastic wall 102 at step 23. Applying the supplemental material 125 in this way (after being fully dried) may for example be useful with some materials 120, 125 to achieve the desired configuration of the second protrusion 140.

In each of the methods 2, 3, 4, and 5, it may be preferred to apply the supplemental material 125 in step 23 in cross-sectional alignment with at least one of the indentations 115 such that the resulting first and second protrusions 130, 140 are in cross-sectional alignment. This may be accomplished, for example, by mapping the indentations 115 into computer memory and controlling the applicator to align with the mapped indentations, by sensing the indentations and controlling the applicator to align with the sensed indentations, or by mechanically tuning the applicator to the desired alignment. As noted above, FIGS. 10a and 10b show cylindrical first and second protrusions 130, 140 in cross-sectional (and axial) alignment, and FIGS. 11a through 11c show a wave-shaped first protrusion 130 and cylindrical second protrusions 140 in cross-sectional alignment. And, as shown in FIGS. 10b and 11c, the supplemental material 125 may be applied such that an axis 141 or centerline of the second protrusion 140 is generally perpendicular to the second face 102b. Nevertheless, the supplemental material 125 may in other embodiments be applied in step 23 in cross-sectional misalignment with the former indentations 115 to result in misaligned protrusions 130, 140. Producing misaligned protrusions 130, 140 may be less costly due to the reduced precision required in manufacturing compared to manufacturing aligned protrusions 130, 140, and may in some embodiments still result in increased resonance transfer relative to the prior art.

While the methods 2, 3, 4, and 5 apply the supplemental material 125 to create the second protrusion 140, other embodiments may create the second protrusion 140 (step 20 in the method 1) through other processes. For example, some of the elastic compound 120 removably adhered to the former 110 may be drawn away from the former 110, such as by using suction, by spinning the former 110, or by including ferromagnetic particles in the elastic compound 120 and applying targeted magnetic fields (i.e., electromagnetically) to draw the desired amount and configuration of the elastic compound 120 away from the former 110. As another example, the elastic compound 120 removably adhered to the former 110 may be stamped to create the protrusion 140.

And, while the methods discussed above refer to the former 110 being dipped into elastic compound 120, some embodiments may utilize a sheet or particles of elastic compound 120 being heat-shrunk to the former 110 to form the wall 102 and the first protrusions 130. Then the second protrusions 140 would be created using the supplemental material 125 as described above. Utilizing this heat-shrink method may allow increased protrusion density as the material shrinks (or cures). Increased protrusion density may in some embodiments add sensory and control precision by increasing granularity resolution of motion transfer through the wall 102. This may be particularly beneficial as an improved form of conformal coating for electronic subsystems such as sensors, vibrating subsystems, biocompatibility for delicate integrated circuits that may be mounted on living surfaces or implanted within living creatures, and chemical compatibility to harsh environments for sensors and control actuators in applications such as robotic subsystems.

In use, the barrier product 100 is worn by a user, for example with the second face 102b (and thus the second protrusions 140) against the user's skin. As the face 102a contacts an external surface, and especially in a non-perpendicular manner, the first protrusion 130 receives a rotational input force and in turn rotates, creating a rotational output force on the second protrusion 140 and enhancing the resonance transfer to the user. The user may thus sense the movement of the second protrusion 140, strengthening the tactile experience. To maximize the tactile experience, the protrusions 130, 140 may be strategically placed to interact with sensitive areas of the user's skin, and in some embodiments may be placed throughout the faces 102a, 102b. And resonance transfer may be greatest if the protrusions 130, 140 are in cross-sectional alignment. It may be particularly desirable in some embodiments for resonance transfer to be tuned such that forces are transferred through the first and second protrusions 130, 140 (and the wall 102) with minimal losses.

As noted above, ferromagnetic particles may be dispersed in the elastic compound 120 for manufacturing purposes. Yet even if not used for manufacturing purposes, it may be desirable in some embodiments to include ferromagnetic particles (e.g., polymerized fullerene chains and networks) in the elastic compound 120 and/or the supplemental material 125. Ferromagnetic material in the second protrusions 140, for example, may cause the second protrusions 140 to move relative to the wall 102 when appropriate magnetic fields are induced near the barrier product 100 (e.g., condom 100"); and movement of the second protrusions 140 may create output forces on the first protrusions 130, causing the first protrusions 130 to rotate and thereby add additional movement and sensation at both sides of the wall 102. Due to the resonance transfer between the first and second protrusions 130, 140, the elastic compound 120 need not include the ferromagnetic particles to achieve magnetic reactivity if the supplemental material 125 includes the ferromagnetic material. Said differently, in use, physical and/or electromagnetic waveforms may be transferred through (or along the surface of) a substrate utilizing matched or mating transfer elements (protrusions) to efficiently vibrate (or otherwise move) the transfer elements structured to a wavelength that is naturally optimal for energy transfer at select frequencies. This may be referred to as isomorphic planar resonance, and strategic distribution of element patterns may allow discrete selective transfer per element along and through a common plane.

Similarly, piezoelectric particles (or other reactive particles which move when exposed to targeted radio frequencies, whether in audible or inaudible wavelengths) may be included in the elastic compound 120 and/or the supplemental material 125. Piezoelectric particles in the second protrusions 140, for example, may cause the second protrusions 140 to move relative to the wall 102 when appropriate radio frequencies are transmitted to the barrier product 100 (e.g., condom 100"); and movement of the second protrusions 140 may create output forces on the first protrusions 130, causing the first protrusions 130 to rotate and thereby add additional movement and sensation at both sides of the wall 102. Due to the resonance transfer between the first and second protrusions 130, 140, the elastic compound 120 need not include the reactive particles to achieve RF reactivity if the supplemental material 125 includes the reactive particles. Targeted radio frequencies can be propagated and therefore directly and/or indirectly conducted through electromagnetic waves, air, liquid, or solid surfaces.

In some embodiments, particles which react to chemical stimuli by moving may be included in the elastic compound 120 and/or the supplemental material 125. These reactive particles in the second protrusions 140, for example, may cause the second protrusions 140 to move relative to the wall 102 when exposed to the chemical stimuli; and movement of the second protrusions 140 may create output forces on the first protrusions 130, causing the first protrusions 130 to rotate as well. This may provide a tactile indicator, for example, when an undesired chemical stimulus is encountered, or may add movement and sensation when a desired chemical stimulus is encountered. Due to the resonance transfer between the first and second protrusions 130, 140, the elastic compound 120 need not include the reactive particles to achieve reactivity if the supplemental material 125 includes the reactive particles.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention. It will be understood that certain features and subcombinations are of utility and may be employed without reference to other features and subcombinations and are contemplated within the scope of the claims. The specific configurations and contours set forth in the accompanying drawings are illustrative and not limiting. Some steps may be performed in different orders than described herein.

The invention claimed is:

1. A method for creating a barrier product, the method comprising the steps:
   (a) dipping a former into a tank of elastic compound, the former having an outer surface and an indentation, the indentation extending inwardly from the outer surface for creating a first protrusion on a first face of the barrier product;
   (b) removing the former from the tank of elastic compound, whereby some of the elastic compound removably adheres to the former, a portion of the removably adhered elastic compound filling the indentation;
   (c) at least one of:
      (1) mapping the indentation into computer memory; and
      (2) sensing the indentation;
   (d) applying supplemental material to the elastic compound removably adhered to the former, whereby creating a second protrusion on a second face of the barrier product; and
   (e) fully drying the supplemental material;
   wherein applying supplemental material in step (d) comprises applying as least part of the supplemental material as a cylinder, the cylinder having an axis generally perpendicular to the second face; and
   wherein applying supplemental material in step (d) comprises at least one of:
      (1) controlling an applicator to apply the supplemental material in cross-sectional alignment with the former indentation using the mapping in the computer memory, whereby the first protrusion is aligned with the second protrusion; and
      (2) controlling an applicator to apply the supplemental material in cross-sectional alignment with the former indentation using the sensing, whereby the first protrusion is aligned with the second protrusion.

2. The method of claim 1, further comprising the steps:
   (i) partially drying the removably adhered elastic compound; and
   (ii) fully drying the removably adhered elastic compound;
   wherein step (i) occurs before step (d), and wherein step (ii) occurs after step (d).

3. The method of claim 1, further comprising the steps:
   (i) partially drying the removably adhered elastic compound; and
   (ii) fully drying the removably adhered elastic compound;
   wherein step (i) occurs before step (d), and wherein step (ii) occurs before step (d).

4. The method of claim 1, further comprising the step:
   (i) partially drying the supplemental material;
   wherein step (i) occurs before step (d).

5. The method of claim 1, wherein applying supplemental material in step (d) comprises projecting the supplemental material onto the removably adhered elastic compound with an applicator such that the applicator does not touch the removably adhered elastic compound.

6. The method of claim 5, further comprising the step:
   (i) partially drying the supplemental material;
   wherein step (i) occurs before step (d).

7. The method of claim 1, wherein at least part of the indentation has a cylindrical configuration.

8. The method of claim 1, wherein the elastic compound includes at least one item selected from the group consisting of latex, polyurethane, polyisoprene, nitrile rubber, polyvinyl chloride, silicone, and neoprene.

9. The method of claim 8, wherein the composition of the supplemental material is the same as the composition of the elastic compound.

10. The method of claim 9, further comprising the steps:
(i) partially drying the removably adhered elastic compound; and
(ii) fully drying the removably adhered elastic compound;
wherein step (i) occurs before step (d), and wherein step (ii) occurs after step (d).

11. The method of claim 10, further comprising the step:
(iii) partially drying the supplemental material;
wherein step (iii) occurs before step (d).

12. The method of claim 9, further comprising the steps:
(i) partially drying the removably adhered elastic compound; and
(ii) fully drying the removably adhered elastic compound;
wherein step (i) occurs before step (d), and wherein step (ii) occurs before step (d).

13. The method of claim 12, further comprising the step:
(iii) partially drying the supplemental material;
wherein step (iii) occurs before step (d).

14. The method of claim 1, wherein the barrier product is a condom.

15. A method for creating a barrier product, the method comprising the steps:
(a) dipping a former into a tank of elastic compound, the former having an outer surface and an indentation, the indentation extending inwardly from the outer surface for creating a first protrusion on a first face of the barrier product;
(b) removing the former from the tank of elastic compound, whereby some of the elastic compound removably adheres to the former, a portion of the removably adhered elastic compound filling the indentation;
(c) at least one of:
(1) mapping the indentation into computer memory; and
(2) sensing the indentation;
(d) producing a second protrusion on a second face of the barrier product, the second protrusion being in cross-sectional alignment with the first protrusion; and
(e) fully drying the elastic compound;
wherein step (a) is performed before step (b), step (b) is performed before step (d), and step (d) is performed before step (e); and
wherein the elastic compound includes ferromagnetic particles, and wherein producing a second protrusion in step (d) comprises electromagnetically drawing some of the removably adhered elastic compound away from the former using at least one of:
(1) the mapping in the computer memory; and
(2) the sensing.

16. The method of claim 15, wherein the barrier product is a condom.

* * * * *